United States Patent [19]

Gross

[11] Patent Number: Plant 7,734

[45] Date of Patent: Dec. 3, 1991

[54] POINSETTIA NAMED GROSTAR

[76] Inventor: Bruno Gross, "Le Bois" Angeac Champagne, 16130 Segonzac Charente, France

[21] Appl. No.: 446,882

[22] Filed: Dec. 6, 1989

[51] Int. Cl.[5] ..... A01H 5/00
[52] U.S. Cl. ..... Plt./86
[58] Field of Search ..... Plt./86

[56] References Cited

U.S. PATENT DOCUMENTS

P.P. 6,592 2/1989 Gross ..... Plt. 86

*Primary Examiner*—James R. Feyrer
*Attorney, Agent, or Firm*—Jordan and Hamburg

[57] ABSTRACT

A new Poinsettia cultivar distinguished by large, bright red bracts, large, thick stems and leaves and a short growth habit is herein described. The stems of this plant are noticeably strong with short internodes, yet possessing a strong self-branching habit. As a flowering potted plant, it performs equally well as a single-stemmed, unpinched plant or a branched, pinched plant.

1 Drawing Sheet

BACKGROUND OF THE NEW PLANT

This new Poinsettia originated as a seedling and was produced by me in my greenhouses in Le Bois d'Angeac, France. I selected this plant because of its large bright red bracts, thick green leaves and thick red bracts, short growth habit, thick, strong stems and self-branching characteristics. This new Poinsettia flowers equally well as either a pinched, multiple branched plant or as an unpinched single stem plant. The plant's characteristics are unique, resulting in a plant which is recognizable as being different from any other poinsettia cultivar. I propagated this new plant by vegetative cuttings through successive generations, which time and again has shown its thick stems and leaves, short stature and bright red bracts which have remained unchanged from generation to generation.

DESCRIPTION OF THE DRAWING

My new variety of Poinsettia is illustrated by the accompanying full color photographic drawing, the color being as true to that herein specified as is reasonably possible to obtain by conventional photographic procedures.

DESCRIPTION OF THE NEW PLANT

The following is a detailed description of this new poinsettia as observed under greenhouse culture in Le Bois d'Angeac, France. Color designations are according to The R.H.S. Colour Chart published in 1966 by The Royal Horticultural Society at London, England.

THE PLANT

Origin: Cross breeding of our own variety No. 51×our own variety No. 222.

Classification:

*Botanic.—Euphorbia pulcherrima.*

Form: Shrub.

Height: Typically 135 cm after one year.

Growth habit: As a single stem, upright, but short. Leaves and bracts are unusually thick and large. The stems are thick and strong with closely spaced nodes. I observed flowering stems of 30–35 cm length with red bract presentations 30–40 cm in diameter.

Branching: Upright with many stems producing a compact, bushy plant full in appearance.

Growth rate: Very fast. No growth regulator is needed. Rooting of vegetative cuttings occurs in 15–20 days under intermittent mist and the plant will flower in about 8 weeks under continuous long night conditions and night temperatures of 16°–18° C. The number of branches presented after pinching is normally 6–8.

Foliage: This plant has unusually large, thick and erect leaves having a brilliant green upper side and a light green underside, with the plane of the leaf blade nearly perpendicular to the stem. There is no leaf torsion. The leaves have no hair. The length from the apex to the base of an average leaf is 5.5 cm and the width thereof at the widest point is 13 cm. The larger leaves typically have leaf blades 14–16 cm long and 10–12 cm wide and leaf petioles 6–7 cm long. The length from the leaf base to the petiole base is typically 3.2 cm. The color of the petiole surface is reddish.

Leaf shape: Typical mature leaves are lanceolate in overall shape, the apex of a mature leaf being acuminate in shape and the base thereof being ovate in shape. Torsion is absent in the mature leaf.

Bracts: Generally there are 12 uniformly colored bright red bracts, typically thicker and larger than most poinsettia cultivars. Bract color is very stable. Flower parts and bracts are retained 4 to 6 weeks. It is not unusual for the larger bract-leaf blades to be 16–18 cm long and 10–13 cm wide with short leaf petioles, 3–4 cm long, which are reddish in color. The short bract petioles result in a bract presentation with a close, tight center. The large lower bracts are somewhat cascading while the plane of the smaller bract blades is nearly perpendicular to the stem axis.

Shape: In overall shape, the bracts are usually ovate with entire margins and have an acute apex and a rotundate base.

Color:

*Upper side.*—RHS 50A.
*Under side.*—RHS 46D.

The cyathia are very large and always have one nectar cup. The cyathia keeps very long, more than four weeks. The coloration of the cyathia is yellow-orange, and the cyathia exude very strongly.

I claim:

1. A new and distinctive Poinsettia cultivar, substantially as herein shown and described, particularly distinguished by large, bright red bracts, large thick stems and leaves and a short, self-branching growth habit.

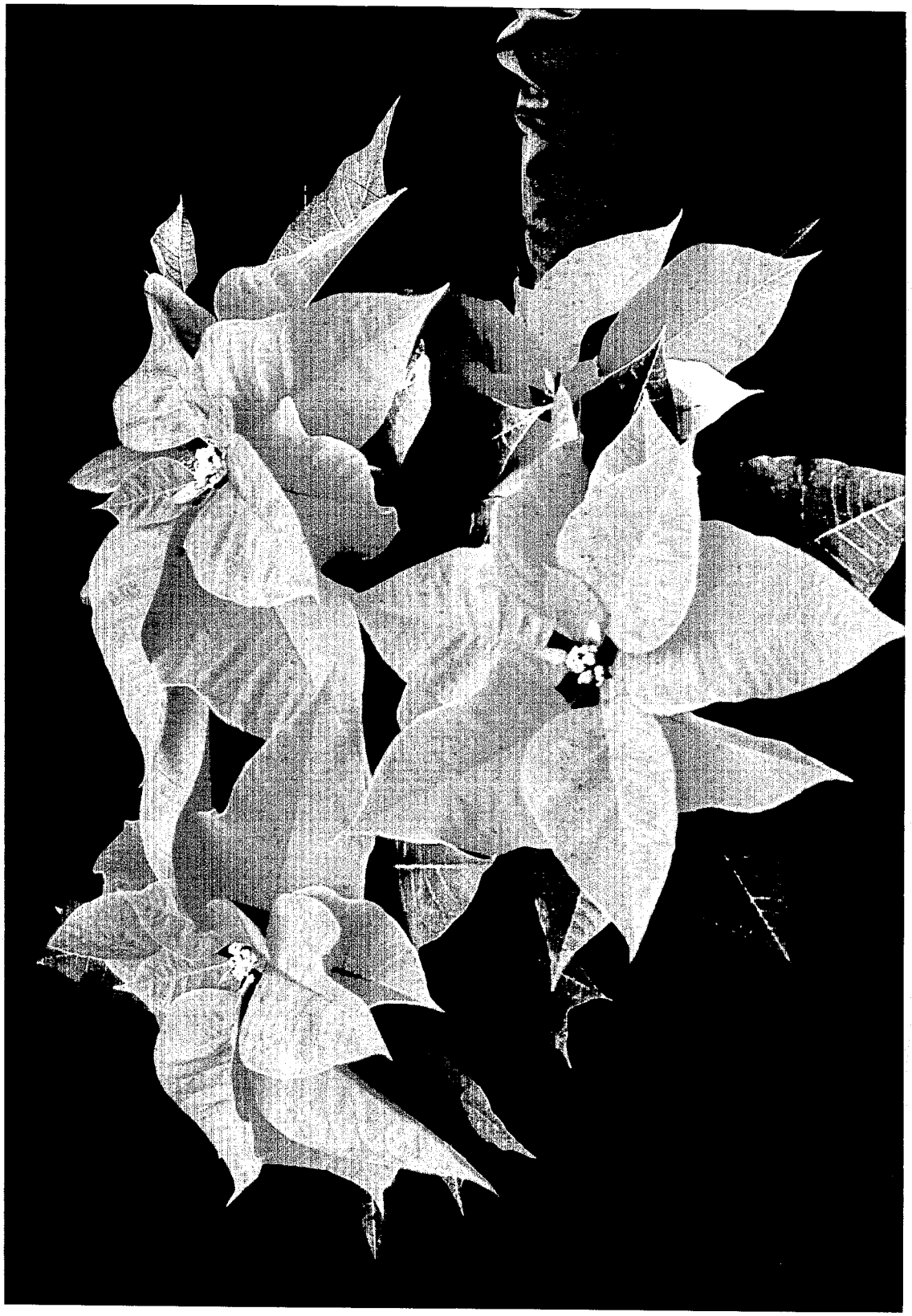

* * * * *